Dec. 9, 1941. M. T. BARCAFER Plant Pat. 493
IVY PLANT
Filed June 23, 1941
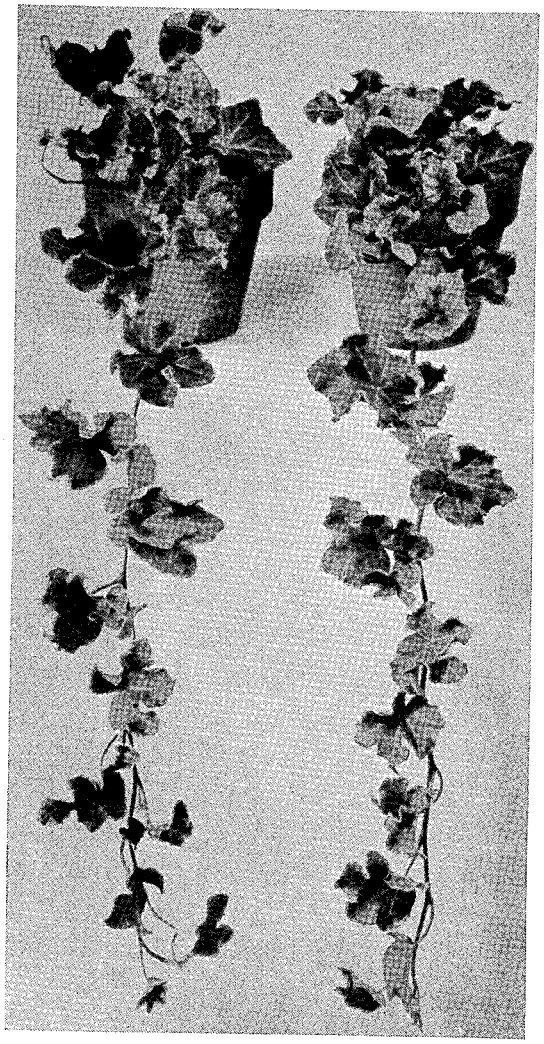
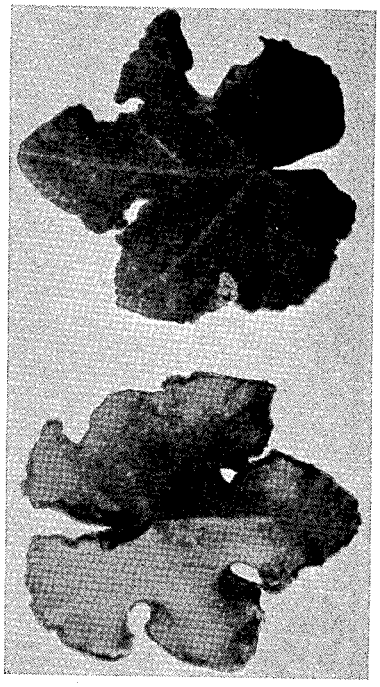
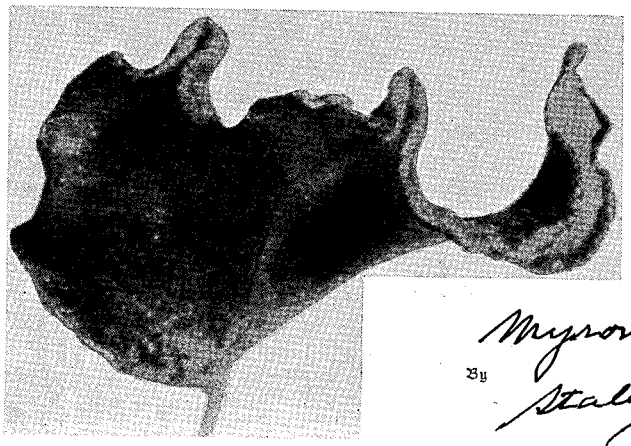
Inventor
Myron T. Barcafer
By Staley & Welch
Attorneys Patented Dec. 9, 1941

Plant Pat. 493

UNITED STATES PATENT OFFICE

493

IVY PLANT

Myron T. Barcafer, Springfield, Ohio

Application June 23, 1941, Serial No. 399,293

1 Claim. (Cl. 47—59)

This invention or discovery relates to ivy plants, asexually reproduced, it particularly relating to a new and distinct variety of ivy plant (*Hedera helix*), the leaves of which have a formation which imparts to the same a new and distinct appearance.

The plant is a sport grown from a cutting originally produced from the variety of ivy plant known as Marion Beauty. The plant is of the pendulum form having self-branching characteristics and a rapid growth. The leaves are in color substantially of the usual ivy green or evergreen, the leaves having usually five lobes. The dimensions of the leaves vary substantially from 1½″ x 1½″ for the smaller leaves to 2″ x 2″ for the larger leaves, the illustrations of the single leaves being slightly enlarged.

The accompanying illustration at the left shows two ivy plants having the new and distinct characteristics of the invention or discovery. The upper illustration at the right hand side of the sheet is a view of one of the leaves, while the illustration immediately beneath it is a view of the same leaf looking at the reverse side thereof. The view at the bottom of the sheet is in perspective of another one of the leaves of the plant looking at the under side of the leaf and the edges of the lobes.

The novel characteristic resides in the formation of the leaves. The edges of the lobes of the leaves have a crimped appearance and roll underneath so as to impart to the edges a rolled or beaded effect. The growth of the beads or rolls between the lobes causes an expansion of the edges of those portions of the lobes, causing the leaf to buckle and present a wavy appearance.

Having thus described my invention or discovery, I claim:

A new and distinct variety of ivy characterized by leaves each having a plurality of lobes, the edges of the lobes presenting a crimped appearance on the upper side of the leaf and having a rolled or beaded effect on the reverse side of the leaf, the leaves after reaching maturity each presenting a wave-like appearance.

MYRON T. BARCAFER.